United States Patent
Suck et al.

(10) Patent No.: US 6,900,034 B2
(45) Date of Patent: May 31, 2005

(54) METHOD FOR PURIFYING RECOMBINANT PROTEINS EXPRESSED AS INSOLUBLE AGGREGATES

(75) Inventors: Roland Suck, Hamburg (DE); Oliver Cromwell, Wentorf (DE); Helmug Fiebig, Schwarzenbek (DE)

(73) Assignee: Merck Patent GmbH, Darmstadt (DE)

( * ) Notice: Subject to any disclaimer, the term of this patent is extended or adjusted under 35 U.S.C. 154(b) by 2 days.

(21) Appl. No.: 10/363,788

(22) PCT Filed: Aug. 18, 2001

(86) PCT No.: PCT/EP01/09552

§ 371 (c)(1),
(2), (4) Date: Mar. 7, 2003

(87) PCT Pub. No.: WO02/20559

PCT Pub. Date: Mar. 14, 2002

(65) Prior Publication Data

US 2003/0170815 A1 Sep. 11, 2003

(30) Foreign Application Priority Data

Sep. 8, 2000 (DE) .......................................... 100 44 360

(51) Int. Cl.$^7$ ............................ C12P 21/06; C07K 1/30; C07K 1/16
(52) U.S. Cl. ........................ 435/69.1; 530/417; 530/419
(58) Field of Search .......................... 435/69.1; 530/417, 530/419

(56) References Cited

U.S. PATENT DOCUMENTS

2002/0018779 A1 * 2/2002 Valenta et al. ........... 424/184.1

FOREIGN PATENT DOCUMENTS

EP 0432419 6/1991
WO WO 9814467 4/1998

OTHER PUBLICATIONS

Ferreira, F. et al. "Purification and Characterization of Recombinant Bel v 1, the Major Birch Pollen Allergen." Journal of Biological Chemistry, vol. 268, No. 26, pp. 19574–19580 (1993).*

Fischer, B. "Renaturation of Recombinant Proteins Produced As Inclusion Bodies." Biotech Adv. vol. 12, pp. 89–101 (1994).*

Lorenz A R et al., "Recombinant food allergens," Journal of Chromatography, May 25, 2001, pp. 255–279, Amsterdam.

* cited by examiner

*Primary Examiner*—Karen Cochrane Carlson
*Assistant Examiner*—Anand Desai
(74) *Attorney, Agent, or Firm*—Millen, White, Zelano & Branigan, P.C.

(57) ABSTRACT

The invention relates to a method for solubilising and purifying recombinant proteins which are expressed in bacterial host cells and are deposited as insoluble aggregates (inclusion bodies). The purification is based on conversion of the inclusion bodies into soluble forms using organic denaturing reagents and using chromatographic methods. Inorganic, alkaline, salt-containing eluents are selected here which, after purification is complete, enable the recombinant proteins, after neutralisation, to be made available in a form which can be employed directly for medical use and is physiologically acceptable. The method is particularly suitable for purifying allergens and allergen fragments.

14 Claims, No Drawings

METHOD FOR PURIFYING RECOMBINANT PROTEINS EXPRESSED AS INSOLUBLE AGGREGATES

PRIORITY DATA

This application is a National stage under 35 U.S.C. § 371 of PCT/EP01/09552 filed Aug. 18, 2001, which claims the benefit under 35 U.S.C. § 119(a)–(d) of German application 100 44 360.5 filed Sep. 8, 2000.

The invention relates to a method for solubilising and purifying recombinant proteins which are expressed in bacterial host cells and are deposited as insoluble aggregates (inclusion bodies). The purification is based on conversion of the said inclusion bodies into soluble forms using organic denaturing reagents and using chromatographic methods. Inorganic, alkaline, salt-containing eluents are selected here which, after purification is complete, enable the recombinant proteins, after neutralisation to be made available in a form which can be employed directly for medical use and is physiologically acceptable. The method is particularly suitable for purifying allergens and allergen fragments.

The method according to the invention is carried out under conditions which are necessary for pharmaceuticals (GMP). The pharmaceutical active ingredients can be used directly, after solubilisation, as parenteral preparations. The preferred recombinant allergens or allergen variants prepared by the method according to the invention can be used both for improved therapy and also for diagnosis of allergic diseases.

It is a general problem in the preparation of recombinant proteins by bacterial or prokaryotic host cell, such as for example, E. coli, that the expressed proteins do not have the correct or native folding that they generally require in order to exhibit full biological activity. The incorrect folding frequently results in the a series of proteins being only in a form which is soluble in the expression medium or are deposited in the form of aggregates, which have come to be known in the scientific literature as so-called "inclusion bodies". The formation of the said "inclusion bodies" has an adverse effect on the purification and requisite soluble availability of the expressed recombinant protein (Marston et al., 1986, Biochem J. 240: 1–12). In order to be able to purify the recombinant proteins deposited in bacteria, denaturing substances, such as, for example, urea or guanidinium hydrochloride, are frequently added to chromatographic eluents. However, these additives cannot be combined with every separation principle, such as, for example, hydrophobic interaction chromatography. Moreover, the products may be modified in a disadvantageous manner by chemical reactions, such as, for example, by cyanate, which can form in urea solutions. Removal of the denaturing agent and thus possible renaturing is usually carried out by dialysis, diafiltration or gel filtration. These processes are not only protracted, but also frequently result in re-precipitation of the products. Analytical detection of complete removal of the above-mentioned denaturing agents in the final product is difficult. The problem described above is particularly important in the preparation and purification of recombinant allergens and allergen variants.

Type 1 allergies have increased dramatically worldwide in recent decades. Up to 20% of the population in industrialised countries suffers from complaints such as allergic rhinitis, conjunctivitis or bronchial asthma, which are caused by allergens present in the air (aeroallergens), which are released by various sources, such as plant pollen, mites, mammals (cats, dogs, horses) and mould fungi. Severe allergies can also be triggered by insect stings, such as, for example, from bees and wasps.

The substances which trigger type 1 allergy are proteins, glycoproteins or polypeptides. After uptake via the mucous membranes or after stings, these allergens react the IgE antibodies bonded to the surface of mast cells in sensitised persons. If two or more IgE antibodies are linked to one another through an allergen, this results in the secretion of mediators (for example histamine, prostaglandins) and cytokines by the effector cell and thus in triggering of the allergic symptoms. With the aid of cDNA sequences, it is possible to prepare recombinant allergens which can be used in the diagnostics and therapy of allergies (Scheiner und Kraft, 1995, Allergy 50, 384–391). Recombinant allergens can achieve particular importance in diagnostic methods which, compared with conventional extracts, enable the identification of individual IgE sensitisation spectra. In addition, specific genetic-engineering modifications to the recombinant allergens are possible, enabling a reduced allergenic potential to be achieved with unchanged reactivity with the regulatory T helper cells (Schramm et al., 1999, J. Immunol. 162 (4): 2406–2414; Valenta et al., 1999, Biol. Chem. 380: 815–24; Singh et al., 1999, Int. Arch. Allergy Immunol. 119: 75–85). Allergen variants of this type are promising future candidates for specific immunotherapy of type 1 allergy. In particular, the latter modified allergens are the subject-matter of the method according to the invention.

In this connection, the production of recombinant allergens and allergen variants in the bacterial expression systems frequently used is of particular importance. Compared with eukaryotic systems, these systems offer the advantage that high product yields are obtained after only a short expression time. In addition, they are substantially riskless from a pharmacological point of view with respect to viral contamination and oncogens. However, in their recombinant preparation in bacterial expression systems, the main allergens from various sources, such as, for example, the group 1 (Vrtala et al., 1996, J. allergy Clin. Immunol. 97: 781–7) and 13 (Suck et al., 2000, Clin. Exp. Allergy 30: 324–332) grass pollen allergens, the Der f 2 mite allergen (Iwamoto et al., 1996, int. Arch. Allergy Immunol. 109: 356–61) and the phospholipase A2 and hyaluronidase insect toxin allergens (Soldatova et al., 1998, J. Allergy Clin. Immunol. 101: 691–8; Kuchler et al., 1989, Eur. J. Biochem. 184: 249–254), are deposited in the host cell as inclusion bodies. The allergen variants, such as, for example, fragments and multimers of the main birch pollen allergen Bet V1 (fragment A, fragment B, Bet V1 trimer), also behave in this way, although the unmodified recombinant Bet v1 allergen is substantially soluble (Hoffmann-Sommergruber et al., 1997, Prot. Expr. Purific. 9:233–39; van HageHamsten et al., 1999, J. Allergy Clin. Immunol. 104: 969–7).

The object was thus to provide a method which enables the purification of recombinant proteins in the form of "inclusion bodies", in particular allergens, or proteins with an allergenic action, in a simple and effective manner while avoiding the above-mentioned disadvantages of the methods of the prior art. In addition, the object was to isolate the proteins in such a way that they are, during and in particular at the end of the purification, in a form which enables them to be made available, directly and without further processing, for medical or diagnostic use.

The present invention is a biochemical purification method which leads via an efficient one- or multistep, preferably one-to three-step, purification method, from recombinant proteins which are in the form of inclusion bodies after expression to pure forms of the proteins using essentially unbuffered alkaline eluents.

The invention is also a method in which the recombinant proteins subsequently remain in solution through rapid neutralisation after the final purification step. At the same time, a physiological medium is thereby produced.

The method is particularly optimised for the preparation of recombinant allergens and allergen variants. The method represents a general application for these primary expression products. Allergens and allergen variants from other origins expressed primarily as inclusion bodies can thus also be purified, renatured and formulated by the method.

For the purposes of the invention, the term allergen variants is taken to mean fragments, multimers, such as, for example, dimers or trimers, but also modifications of the original allergens or fragments/multimers thereof. For the purposes of the invention, the latter have insertions, deletions or substitutions of one or more amino acids.

Use is preferably made of recombinant allergen variants which do not occur in nature and which have no or reduced IgE activity, but preserved T-cell activity. The method is particularly suitable for the isolation of the allergen variants of the main birch pollen allergen Bet v 1, namely recombinant fragments A (amino acid 1–74) and B (amino acid 75–164), and of a recombinant trimer. Recombinant allergens and allergen variants prepared by this method are eminently suitable for use for the specific immunotherapy and diagnostics of allergic diseases.

The invention thus relates to methods for the preparation of purified, recombinant proteins in soluble, biologically active form as a physiological medium which is directly suitable for medical use from protein aggregates ("inclusion bodies") obtained after bacterial expression which are insoluble in the expression medium, which method can be described by the following steps:

(i) uptake of the separated-off insoluble protein aggregates in organic denaturing reagents, (ii) purification of the solution from (i) by means of at least one chromatography step using essentially inorganic unbuffered alkaline, salt-containing eluents, and (iii) neutralisation of the alkaline solution obtained after the final purification step which contains the dissolved, renatured and biologically active protein.

For the purification, the insoluble aggregates formed primarily are firstly dissolved in denaturing reagents known per se and thereby denatured. Preference is given to the use of urea, in particular 5 to 10 M urea, preferably 8 M urea. Alternatively, other agents, such as, for example, relatively highly concentrated sodium or potassium hydroxide solution (0.2 M to 1 M) or the above-mentioned guanidinium hydrochloride, can also be used.

In a further step, the dissolved, denatured protein is bonded to a suitable, chromatographic material. Primarily suitable here are ion exchangers, preferably anion exchangers.

The chromatography eluent employed in accordance with the invention is an essentially inorganic unbuffered, alkaline, salt-containing solution. Suitable eluents are solutions of, for example, NaOH or KOH together with NaCl or KCl. If desired and in a preferred embodiment, sodium hydrogencarbonate or potassium hydrogencarbonate is added to the eluent for the possibility of pH reduction. Preferred eluents contain NaOH, NaCl, or NaOH, NaCl and $NaHCO_3$. The aqueous alkaline solution has in accordance with the invention a content of NaOH or KOH of from 5 mM to 50 mM (mol/l), preferably from 15 to 25 mM, in particular 20 mM. The salt concentration (for example NaCl) is relatively low at the beginning, so that the protein bonds strongly to the ion exchanger material. Initial salt concentrations according to the invention are between 5 and 50 mM, preferably between 15 and 30 mM, in particular 20 mM. This removes the denaturing agent and impurities which do not bond or do not bond sufficiently strongly to the chromatography material. If NaHCO3 is added, this has a content of from 5 to 15 mM, preferably 11 mM.

Thus, the invention thus relates to a corresponding method in which the denaturing reagent is removed from the denaturing solution by bonding the dissolved recombinant protein to a chromatography material and exchanging the denaturing solution for an essentially inorganic unbuffered, alkaline eluent which has a salt concentration which ensures bonding of the protein to the said exchanger material.

In order to elute the bonded recombinant protein, a higher salt concentration (NaCl or KCl) is provided successively in accordance with the method according to the invention by means of a gradient with the other conditions the same. A linear gradient of between about 20 mM NaCl (KCl) (start value) and 0.5 M NaCl (end value) is preferably used. Not only is the desired protein thereby recovered, but it is separated from other impurities (for example other proteins).

The invention thus relates to a corresponding method which is characterised in that the bonded recombinant protein is eluted by increasing the salt concentration and freed from impurities in the process, with the increase in the salt concentration preferably being achieved by means of a gradient.

In some cases, it may be sufficient not to follow this by a further purification step, since the eluted protein is adequately purified in accordance with the requirements. In such cases, the neutralisation step described in greater detail below follows on directly in order to obtain a ready-to-use and active protein.

Otherwise, a further chromatography step is carried out in accordance with the method. All known chromatography methods can in general be employed here. In detail, this will depend on the chemical/physical properties of the particular protein to be purified. Preferably, in particular in the case of allergens and allergen variants of the Bet v 1 type, the further purification is carried out by means of hydrophobic interaction chromatography. Alternatively, gel filtration can also be carried out instead of this.

A preferred embodiment of the method according to the invention is a three-step method which comprises ion exchanger chromatography, hydrophobic interaction chromatography and gel filtration, preferably in the stated sequence. However, this does not mean a restriction of the method according to the invention.

Thus, the invention thus furthermore relates to a corresponding method which has at least one further chromatography step, preferably hydrophobic interaction chromatography and/or gel filtration.

It is essential to the invention in all these purification steps that they work with the same qualitative and quantitative composition of the eluents which has already been described in detail above: NaOH, NaCl and preferably $NaHCO_3$, or the corresponding potassium derivatives. Only the concentration of the sodium chloride component can be arranged in a variable manner in the various steps. Thus, for example, in hydrophobic interaction chromatography, an NaCl (KCl) gradient from high (1–3 M, preferably 2 M) to low (30–10 mM, preferably 20 mM) concentration is employed. The final concentration here was ultimately dependant on the desired salt concentration after the final purification step.

This concentration should in accordance with the invention be the concentration of a physiologically tolerated solution. If, for example, gel filtration is the final purification step in the preferred three-step purification method, approximately 150 mM NaCl is used. Finally, the desired final concentration of salt after the final step can also be controlled by dilution or addition of salt, this in turn being dependent on the amounts of target protein chromatographed.

After the final purification step—gel filtration in the preferred embodiment of the method—the solution is neutralised or the protein renatured by addition of dilute acid, preferably HCl, with the pH being set from 6.5 to 8.0. The solution with the active recombinant protein can now, if necessary after subsequent adjustment of the salt content (for example Na+) and protein content, be employed directly in formulated form.

The invention thus relates to a corresponding method which is characterised in that the neutralisation is carried out in a pH range between 6.5 to 8.0 after purification is complete, with dilute acid, in particular dilute HCl, preferably being employed.

The method according to the invention is described in greater detail below using the example of the isolation of the allergen variants of the main birch pollen allergen Bet v 1, namely recombinant fragments A (amino acid 1–74) and B (amino acid 75–164), and of a recombinant trimer:

For the purification, the primary insoluble aggregates are denatured, preferably in 8 M urea. Alternatively, other agents can also be employed, for example 0.2 M sodium hydroxide solution.

The first chromatographic purification step is carried out by means of anion exchange chromatography, for example on Source Q. In this, most allergens or allergen variants are bonded to the support and transferred into the eluent by the initial denaturing solution. The alkaline eluent causes the proteins to remain in solution. NaCl gradient elution causes partial removal of bacterial impurities and active ingredient fragments.

In two further purification steps, hydrophobic interaction chromatography and gel filtration, the pre-purified and equilibrated allergens or allergen variants are essentially separated from bacterial impurities still remaining. To this end, basically the same eluent substances are used, consisting of low-molecular-weight base and a varying proportion of inorganic salt.

The invention thus relates to a specific eluent system in which the recombinant proteins to be purified are kept in solution under gentle conditions during the purification and which results in effective purification.

After the final chromatography step, the purified recombinant proteins can in accordance with the invention be isolated in soluble form or renatured by simple neutralisation of the base present in the eluent using a corresponding acid. Given a suitable choice of the concentrations of the eluent additives, a physiological solution which is suitable for parenteral preparations is formed. The purified recombinant allergens or allergen variants are identified via their known physical, chemical, immunological or biological properties, in particular by means of isoelectric focusing, SDS-PAGE and specific monoclonal antibodies as well as IgE antibodies of allergy sufferers.

The solvent is tested by pH measurement and quantification of the $Na^+$ and $Cl^-$ and, if desired, $CO^{3-}$ concentration. These methods are generally known and described. The yield of the recombinant allergens or allergen variants purified and solubilised in accordance with the invention is 75–95%, based on the primary starting protein.

The allergen components prepared in this way can be employed in in-vivo and in-vitro diagnostics as part of allergen component-resolving identification of the patient-specific sensitisation spectrum as well as for the specific immunotherapy of allergies. Furthermore, pharmaceutical preparations in the form of depot preparations can be prepared by conversion of the purified recombinant proteins.

A preferred embodiment of the method according to the invention is shown in diagrammatic form below (Table 1):

TABLE 1

Isolation of inclusion bodies
Denaturing, for example in 8 M urea
Anion exchange chromatography, for example Source Q Solution A: 20 mM NaOH, 20 mM NaCl, 11 mM NaHCO$_3$
Solution B: 20 mM NaOH, 0.5 M NaCl, 11 mM NaHCO$_3$
(Optional) hydrophobic interaction chromatography, for example Source PHE Solution A: 20 mM NaOH, 2 M NaCl, 11 mM NaHCO$_3$
Solution B: 20 mM NaOH
(Optional) gel filtration, for example Superdex 75

Solution A: 10 mM NaOH, 11 mM NaHCO$_3$
148.4 mM NaCl
Renaturing 1 formulation

Target protein in 10 mM NaOH, 148.4 mM NaCl, 11 mM NaHCO$_3$ + addition of 100 mM HCl to 10 mM = soluble target protein in 0.154 M Na+ solution In summary, the following can thus be observed: the present invention thus enables, through the method according to the invention made available, which through the specific composition of the chromatography eluents, the choice of chromatography media and the specific setting of the pH and thus the salt content, a technologically and pharmacologically implementable production method for the isolation of highly pure, soluble recombinant allergens and allergen variants which are prepared primarily as insoluble aggregate, which takes little labour and time. Since the conditions under which the recombinant proteins are purified and renatured or solubilised are gentle and pharmacologically suitable compared with known methods, the active ingredients can be employed both for diagnostics and for parenteral therapy of allergic diseases.

EXAMPLE

Isolation of soluble allergen variants of Bet v 1

(therapeutically effective allergen variants of recombinant Bet v 1, fragment A and B and the Bet v 1 trimer)

The inclusion bodies of the allergen variants purified by standard methods are preferably denatured in 8 M urea, 20 mM tris/HCl. After complete denaturing, filtration, preferably 0.22–0.45 μm, or centrifugation, preferably 5–15 min at 10,000–20,000 xg, is carried out. The clarified solution is employed for ion exchange chromatography with Source 15Q (Pharmacia), with the support material being equilibrated with alkaline solution, preferably 20 mM NaOH, 11 mM NaHCO$_3$ and 20 mM NaCl. The support material must be stable at pH values of up to 12.0. The relatively high pH of the starting solution causes virtually all target proteins to bond to the anion exchanger. Exceptions are extremely rare proteins whose isoelectric point is above 11.0. The rinsing of the immobilised proteins with starting solution effectively removes the denaturing solution (for example 8 M urea) and pharmacologically unfavourable buffer substances (for example tris). This method ensures that a change to a solvent which facilitates the subsequent separation steps occurs with retention of the solubility of the recombinant proteins. The subsequent elution is carried out with rising NaCl gradient, for example from 20 mM NaOH, 11 mM NaHCO$_3$20 mM NaCl to 20 mM NaOH, 11 mM NaHCO$_3$, 0.5 M NaCl, and effects separation of impurities (host cell proteins) and active ingredient fragments.

The next, chromatography step is hydrophobic interaction chromatography (only for the fragments). To this end, the eluate from step 1 is adjusted with a high-molarity salt solution, for example 5 M NaCl and 20 mM NaOH, 11 mM NaHCO$_3$, in such a way that the target protein bonds. The elution of the bonded target protein is carried out with low-salt or salt-free alkaline solution, for example 20 mM NaOH. The support employed for the hydrophobic interaction chromatography must likewise be alkali-stable to pH 12, such as, for example, Source PHE.

As the third step, gel filtration, for example Superdex 75, is carried out under alkaline conditions. The chromatography solution is selected in such a way that neutralisation of the base added in the eluent results in the desired final formulation, such as, for example, 10 mM NaOH, 11 mM NaHCO$_3$ and 148.4 mM NaCl.

The eluate from the gel filtration is finally neutralised using an acid corresponding to the base used, by means of which on the one hand a neutral pH is established and the compatible substances, compatibility of a single eluent with diverse separation principles, and the avoidance of protracted and under certain circumstances invalidatable methods such as dialyses. In addition, the sodium hydroxide solution, which is known to be an effective bacteriostatic, prevents the proteins present in it from being degraded or contaminated by microorganisms. Endotoxins, which can cause problems in bacterial expressions, are likewise effectively removed or degraded. The sequence and number of the chromatography steps described above can be changed depending on the specific physiochemical properties of the target proteins. An overview of the solutions is shown in Table 2.

Neutralisation/Solubilisation after Gel Filtration:

slow addition of 1/10 volume (based on the initial mixture) of 100 mM HCl.
for example in 100 ml of starting solution contain:
10 mM NaOH, 148.4 mM NaCl, 11 mM NaHCO3
after neutralisation 110 ml:
11 mM NaHCO3*10/11=10 mM NaHCO3
10 mM NaOH/HCl (NaCl)*10/11=9.1 mM NaCl
148.4 mM NaCl*10/11=134.9 mM NaCl The finished solution is accordingly composed of 154 mM Na$^+$, 144 mM Cl$^{31}$ and 10 mM CO$^{3-}$.

TABLE 2

Solutions for the chromatographic separation of Bet v 1 variants:

| Chromatog./protein | Sample application | Solution A | Solution B | Gradient |
| --- | --- | --- | --- | --- |
| AIEX | | | | |
| Fragment 1 | 8 M urea, 20 mM tris/HCl pH 8.0 | 20 mM NaOH, 10 mM NaCl 11 mM NaHCO$^3$ | 20 mM NaOH, 500 mM NaCl, 11 mM NaHCO$^3$ | 10 CV |
| Fragment 2 | see above | see above | see above | see above |
| Trimer | see above | see above | 20 mM NaCH, 800 mM NaCl, 11 mM NaHCO$^3$ | see above |
| HIC | | | | |
| Fragment 1 | set AIEX pool to 2 M NaCl | 20 mM NaOH, 2 M NaCl, 11 mM NaHCO$^3$ | 20 mM NaOH | 10 CV |
| Fragment 2 | set AIEX pool to 3 M NaCl | 20 mM NaOH, 3 M NaCl, 11 nM NaHCO$^3$ | 20 mM NaOH | 10 CV |
| Trimer | — | — | — | — |
| Gel filtration | | | | |
| Fragment 1 | HIC pool | 10 mM NaOH, 148.4 mM NaCl, 11mM NaHCO$^3$ | — | — |
| Fragment 2 | see above | see above | — | — |
| Trimer | Q pool | see above | — | — |

All solutions and fractions are stored at RT. (CV = column volume).

protein is thus converted into a soluble form or renatured, and on the other hand the desired salt content is established through neutralisation. Thus, for example, a gel filtration solution comprising 10 mM NaOH, 11 mM NaHCO$_3$ and 148.4 mM NaCl is converted into physiological saline solution through addition of 1/10 (v/v) 100 mM HCl. The solvent is tested by simple measurement of the pH and Na$^+$ quantification. In accordance with the invention, the method thus involves minimal sample treatments, short sample standing times, the use of exclusively pharmacologically

What is claimed is:

1. Method for the preparation of a purified, recombinant protein variant of a Bet v1 allergen, wherein said variant is fragment A (amino acid 1–74), B (amino acid 75–164), allergic fragments thereof, or multimers of the Bet v1 allergen, in soluble, biologically active form as a physiological medium which is directly suitable for medical use from protein aggregates (inclusion bodies) obtained after bacterial expression which are insoluble in the expression medium, characterized in that the following steps are carried out:

(i) uptake of the separated-off insoluble protein aggregates in organic denaturing reagents, (ii) purification of the solution from (i) by means of at least one chromatography step using essentially inorganic unbuffered alkaline, salt containing eluents, and (iii) neutralization of the alkaline solution obtained after the final purification step which contains the dissolved, renatured and biologically active protein.

2. Method according to claim 1, characterized in that the denaturing reagent employed is urea or guanidinium hydrochloride.

3. Method according to claim 1, characterized in that the denaturing reagent is removed from the denaturing solution by bonding the dissolved recombinant protein to a chromatography material and exchanging the denaturing solution for an essentially inorganic unbuffered, alkaline eluent which has a salt concentration which ensures bonding of the protein to the said exchanger material.

4. Method according to claim 3, characterized in that the bonded recombinant protein is eluted by increasing the salt concentration and freed from impurities in the process.

5. Method according to claim 4, characterized in that the increase in the salt concentration is carried out by means of a gradient.

6. Method according to claim 3, characterized in that the chromatography material employed is anion exchanger.

7. Method according to claim 3, characterized in that at least one further chromatography purification step is carried out.

8. Method according to claim 7, characterized in that the further chromatography step carried out is hydrophobic interaction chromatography and/or gel filtration.

9. Method according to claim 1, characterized in that the chromatographic eluent employed comprises NaOH, NaHCO3, and NaCl.

10. Method according to claim 1, characterized in that the neutralization is carried out in a pH range between 6.5 to 8.0 after purification is complete.

11. Method according to claim 10, characterized in that HCl is employed for the neutralization.

12. Method according to claim 1, characterized in that the said recombinant protein variant has no or reduced IgE activity, but preserved T-cell activity.

13. Method according to claim 1, characterized in that the said multimers are dimers or trimers.

14. Method according to claim 1, characterized in that the said multimer is a trimer or said fragments are fragments A (amino acid 1-74) or B (amino acid 75-164) of the Bet vl allergen.

* * * * *